United States Patent [19]
Hecht et al.

[11] 3,963,698
[45] June 15, 1976

[54] ALKYLATIONS EMPLOYING IN SITU GENERATION OF DIAZOALKANE ALKYLATION REAGENTS

[75] Inventors: Sidney M. Hecht, Cambridge; John W. Kozarich, Newton, both of Mass.

[73] Assignee: Massachusetts Institute of Technology, Cambridge, Mass.

[22] Filed: Jan. 17, 1974

[21] Appl. No.: 434,142

[52] U.S. Cl. ..................... 260/211.5 R; 260/468 R; 260/469; 260/471 R; 260/478; 260/563 R; 260/568; 260/583 R; 260/609 R; 260/611 R; 260/611 A; 260/612 D; 260/614 R; 260/684; 260/692
[51] Int. Cl.² ........................................ C07B 27/00
[58] Field of Search ...... 260/471 R, 612 D, 211.5 R

[56] References Cited

OTHER PUBLICATIONS

Theilheimer; W., (1966), *Synthetic Methods of Organic Chemistry*, vol. 20, Pub. by S. Karger, N.Y., p. 475 cited.
Vogel; A. I., Practical Organic Chemistry, 3rd Edtn., Pub. by John Wiley of N.Y., (1965), pp. 968 and 973 relied on.

*Primary Examiner*—Richard L. Raymond
*Attorney, Agent, or Firm*—Arthur A. Smith, Jr.; David E. Brook; Martin M. Santa

[57] ABSTRACT

Alkylation processes wherein diazoalkane alkylation reagents are generated in situ and utilized to alkylate substrates are disclosed. These processes utilize the relatively slow base-catalyzed decomposition of an N-alkyl, N-nitrosourea to produce a corresponding diazoalkane alkylation reagent, followed by the much faster reaction between the alkylation reagent and the substrate to be alkylated. Generically, suitable ureas can be represented by the structural formula,

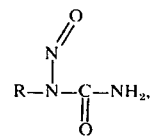

wherein R represents the alkyl moiety to be added to the substrate; R can be alkyl, cycloalkyl, heteroalkyl, aralkyl or heterocyclic.

This process is useful in producing alkylated products without the concomitant disadvantage of building up significant amounts of diazoalkane alkylation reagents during the course of the reaction, many of which have deleterious properties.

21 Claims, No Drawings

ALKYLATIONS EMPLOYING IN SITU GENERATION OF DIAZOALKANE ALKYLATION REAGENTS

The invention described herein was made in the course of or under a grant from the National Science Foundation, an agency of the U.S. Government.

BACKGROUND OF THE INVENTION

1. Field of the Invention

This invention relates to the field of alkylation processes and more particularly to alkylation processes wherein diazoalkane alkylation reagents are generated in situ.

2. Description of the Prior Art.

Many valuable organic syntheses involve alkylation reactions. These include, for example, the alkylation of alcohols and phenols to yield their corresponding ethers; the conversion of thioalcohols to thioethers; the alkylaton of carboxylic acids to yield their corresponding esters; and the alkylation of amines to yield alkylamines. Many other alkylation reactions are known, as well.

Alkylation reactions can be carried out using alkylation reagents, many of which are produced commercially. It appears, however, that usage of many well known alkylation reagents will be significantly restricted in the future, if not prohibited altogether, by imposition of governmental regulations such as those currently in existence or proposed by the Occupational Safety and Health Administration and/or Food and Drug Administration.

Additionally, there are some alkylation reagents which have not been used even without the new restrictions likely to be imposed. It has been known for many years, for instance, that diazoalkanes such as diazomethanes are exceptionally efficient alkylation reagents. Diazomethane is a yellow gas which has been used by the preparation of small quantities as an ethereal solution. The versatility of diazomethane in alkylations can be appreciated by noting that it can be reacted with carboxylic acids to form alkyl esters, or reacted with alcohols to form ethers, or reacted with acid chlorides to produce diazoketones, according to the Arndt-Eistert reaction, which can be decomposed to form carboxylic acids. The foregoing examples are only a few illustrations of the many possible alkylation reactions employing diazomethane, but they do serve to demonstrate its potential value as an alkylation reagent.

Despite this potential, diazomethane has been limited, by and large, to use in laboratory environments because of its many deleterious properties. It is, for example, highly toxic, potentially explosive, and is known tp cause development of specific sensitivity. Because of such properties, users are required to wear heavy gloves and safety goggles, and to work behind safety screens or hooded doors with safety glass. It is also recommended that ground points and sharp surfaces be avoided when using diazomethane as well as exposure to direct sunlight or strong artificial light which are believed to trigger diazomethane explosions. Particular care is also required with organic solvents having boiling points higher than ether so that explosive concentrations of diazomethane do not build up in the vapors above such solutions.

SUMMARY OF THE INVENTION

This invention relates to new alkylation syntheses wherein diazo akylation reagents, such as diazomethane, are generated in situ and consumed in alkylation reactions at rates faster than they are generated. Thus, starting reagents can be combined and alkylations carried out without ever having significant amounts of dangerous alkylation reagents present during the course of the reactions.

These processes involve the relatively slow decomposition of an N-substituted, N-nitrosourea to produce a corresponding diazo-alkylation reagent, followed by a relatively fast reaction between the alkylation reagent and substrate to produce the intended alkylated product. Often, the urea is substituted with an alkyl group such as methyl, and the corresponding alkylation reagent is a diazoalkane such as diazomethane. It should be noted, nevertheless, that the terms "alkyl," "alkylation" and "diazoalkane alkylation reagent" are used for convenience herein in a very broad sense and are intended to encompass such groups as aralkyl groups and heterocyclic groups.

Since decomposition of the urea is base catalyzed, it is often sufficient to react the urea with a conjugate base of the substrate to be alkylated, the conjugate base in this instance also serving as a source of substrate. In some cases, however, the conjugate base of the substrate is a relatively weak base; in these cases, it has been found to be advantageous if a stronger base is added to the reaction mixture to expedite urea decomposition. Because the reaction rate of urea decomposition can be made to be slower than that of the subsequent alkylation of the substrate, significant buildup of a diazoalkane alkylation reagent does not occur.

Such in situ alkylations can be represented in general as follows:

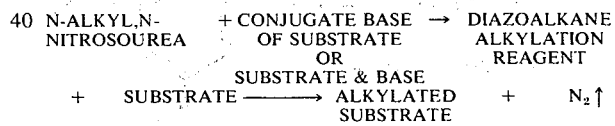

As indicated, N-alkyl,N-nitrosourea is decomposed by the base. Decomposition or deprotonation of the urea produces a diazoalkane alkylation reagent and the substrate, and alkylation proceeds extremely quickly to form the alkylated substrate and nitrogen gas. Since alkylation proceeds relatively quickly contrasted to urea decomposition, no significant amounts of the diazoalkane are ever present.

The methods for in situ generation of diazoalkane alkylation reagents described herein have not been done previously and offer significant advantages over presently available alkylation techniques. For example, alkylated products can be formed in a single reaction vessel to which starting reactants are added. Alkylated products can be removed from the reactor without ever having the presence of significant levels of alkylation reagents during course of the reaction. Also, by-products produced by these in situ alkylations are easily separated; cyanate salts, for example, are formed and can be separated by filtration from organic solvents or by decomposition or separation by ion exchange chromatography or by virtue of their solubility in water. Additionally, these alkylations are convenient syntheses and usually can be carried out in one reactor. Thus, these syntheses represent attractive alternatives to present alkylation reactions, particularly those employing alkylation reagents likely to be restricted.

DESCRIPTION OF PREFERRED EMBODIMENTS

The invention can be methylnitrosourcea, with methylnitrosources, which reacts with basic materials to produce diazomethane. It should be understood, however, that ureas substituted with other alkyl groups could be used as well.

For substrates, i.e., compounds to be alkylated, which are moderately acidic, such as those having a pKa between about 7 and about 16, the conjugate base of the substrate is used. For example, p-nitrophenol can be methylated to form its corresponding methyl ether by reacting its conjugate base, sodium p-nitrophenolate, with N-methyl,N-nitrosourcea in an organic solvent to generate diazomethane, sodium cyanate and p-nitrophenol. The phenol immediately reacts with the diazomethane to form the alkylated either product. Since the generation of diazomethane is relatively slow, no significant concentration of this alkylation reagent is present during the course of the methylation. This reaction can be illustrated as follows:

For more acidic substrates, e.g., those having a pKa of less than about 7, alkylations are preferably carried out starting with the protonated species of the substrate rather than its conjugate base. With such substrates, the conjugate base is so weak that it decomposes the urea only very slowly. Therefore, certain additional bases are added to speed the deprotonation reaction. Bases are chosen which cannot be alkylated themselves, and which can be easily separated from the reaction mixture at the end of the alkylation. Examples of such bases include trialkylamines such as triethylamine, tributylamine, quinuclidine, etc.

A specific illustration of an alkylation employing the addition of external base to deprotonate the urea is the reaction of p-nitrobenzoic acid with N-nitroso,N-methyl urea. The alkylation is carried out in an organic solvent such as 1,2-dimethoxyethane, and triethylamine is added to increase the rate of urea deprotonation. Despite the increased deprotonation speed, this half of the reaction is still relatively slow contrasted to alkylation of the acid by the diazomethane generated. This synthesis produces methyl-p-nitrobenzoate without ever having significant amounts of diazomethane present, and it can be illustrated as follows:

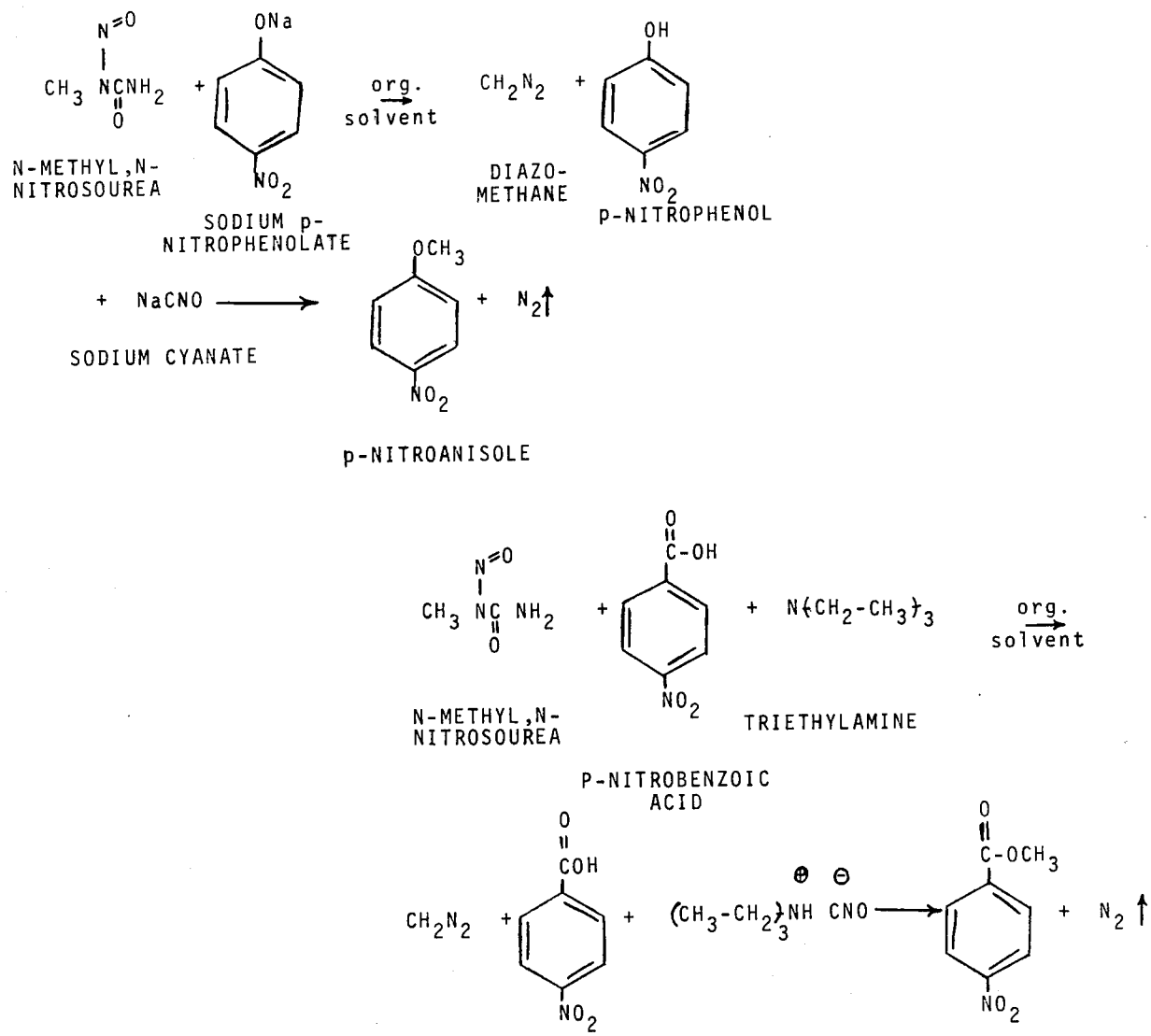

The in situ alkylations described herein are carried out in aprotic neutral solvents which are also inert to the reactants. The alkylnitrosourcea and diazoalkane alkylation reagent must be soluble in the solvent chosen, of course, and it is preferred to choose a solvent in which the final product is soluble and in which the by-products are insoluble. This results in easier separations of products. Typical solvents which can be used, for example, are 1,2-dimethoxyethane, dioxane, ether, tetrahydrofuran, as well as certain aliphatic ethers and hydrocarbons.

If desired, many of these in situ alkylations can also be carried out in mixed systems containing water and miscible organic liquids. This permits the alkylation in good yield of very polar compounds without prior blocking of the reactants to increase solubility of the reaction medium and without the vigorous agitation often required for reactions in two phase systems. Since diazoalkanes react with water, it is only practical to use substrates having a pKa of below about 12 in aqueous media, to assure that the diazoalkane reacts preferentially with the substrate rather than with the aqueous medium.

A specific illustration of a methylation which can be carried out in an aqueous system is the methylation of guanosine. In this alkylation, diazomethane is generated from N-nitroso,N-methylurea in a 1,2-dimethoxyethane/water system; urea decomposition is expedited by the dropwise addition of triethylamine. Guanosine reacts with the diazomethane as soon as it is formed liberating nitrogen, so that no significant concentration of diazomethane is ever built up. Although the diazomethane also reacts with the aqueous phase, the much lower pKa of quanosine. Triethylammonium cyanate is a by-product formed in this reaction, and it can be conveniently decomposed by treatment of the aqueous solution with a cation exchange resin ($H^+$ form) which results in the generation of $CO_2$ and $NH_3$ from the isocyanic acid initially formed. This in situ methylation can be illustrated as follows:

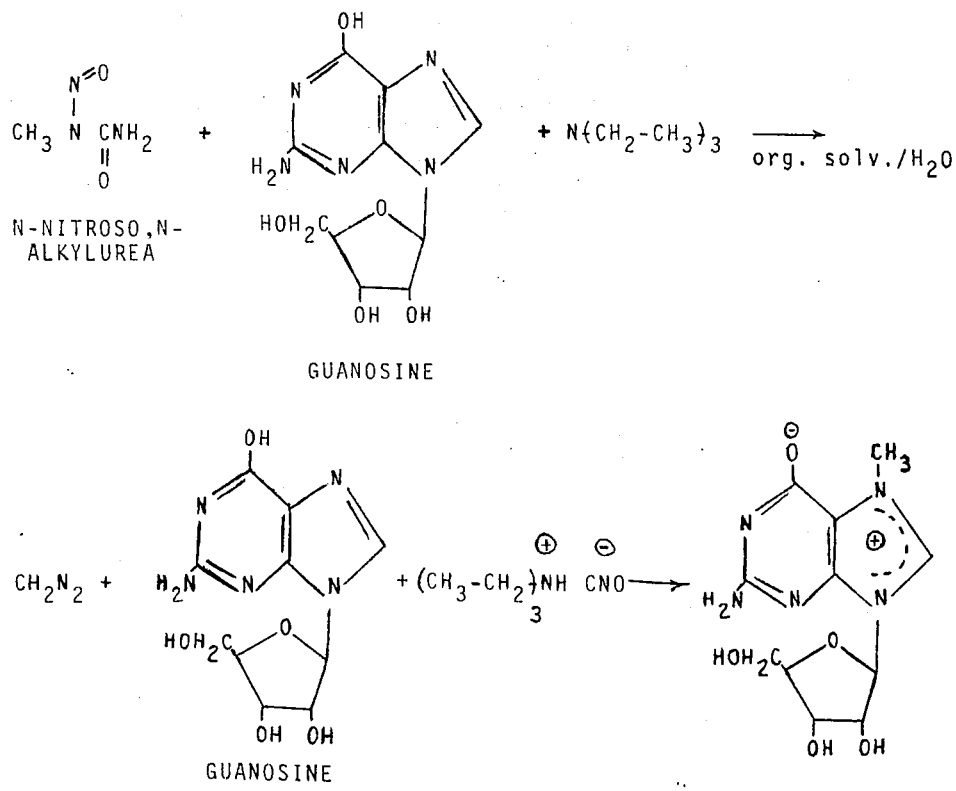

The in situ alkylations described herein depend upon the base-catalyzed decomposition of a N-substituted,N-nitrosourcea to generate diazoalkane alkylation reagents. Suitable N-substituted,N-nitrosoureas can be represented by the structural formula:

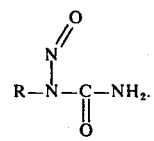

R represents the alkyl group which is to be substituted onto the substrate, and R can be: alkyl, including straight or branched chains and saturated or unsaturated alkyl groups; cycloalkyl; heteroalkyl, i.e., alkyl groups containing heteroatoms such as oxygen; aralkyl, and heterocyclic. Each of these types of groups can be substituted or unsubstituted. R must be, however, a moiety which produces a stable substituted urea which can be deprotonated by a base catalyzed mechanism to produce a stable diazoalkane alkylation reagent.

Specific groups which are suitable include, but are not limited to: alkyls such as methyl, ethyl, propyl, isobutyl, t-butyl, pentyl, hexyl, eicosanyl, 3-chloropropyl, 3-butene, etc.: cycloalkyls such as cyclobutyl, cyclopentyl, cyclohexyl, cyclooctyl, etc.; heteroalkyls such as β-methoxyethyl, β-methoxypropyl, β-methoxybutyl, βethoxyethyl, β-ethoxypropyl, β-ethoxybutyl, etc.; aralkyls such as phenylethyl, phenylpropyl, p-methoxyphenyl, p-methoxyphenylethyl, etc., and, heterocyclics such as tetrahydropyranyl tetrahydrofuranyl, etc., R groups containing heteroatoms are preferably groups having a pKb below about 9 so that the substituted urea is stable. Additionally, the heteroatoms should not be themselves a substrate for alkylation.

A wide choice of substrates or sources of substrates can be chosen for the in situ alkylations described herein. The only constraint upon the selection of a suitable substrate is that deprotonation of the urea can be base catalyzed by the conjugate base of the substrate or by the addition of external base to form the diazoalkane alkylation reagent. It has been found that substrates having a pKa of below about 16 meet these criteria.

The following examples further illustrate the invention. All parts and percentages are by weight, unless otherwise specified.

EXAMPLE 1

In Situ Methylation of Sodium p-Nitrophenolate with N-methyl N-nitrosourea in an Organic Solvent 0.80 grams (5 millimoles) of anhydrous sodium p-nitrophenolate and 0.52 grams (5 millimoles) of N-methyl,N-nitrosourea were added to 25 milliliters of 1,2-dimethoxyethane kept dry with molecular sieves and a drying tube. This mixture was maintained at 0°C. for one hour and then elevated to room temperature for six hours while constant stirring was maintained. Solvent was evaporated and the residue treated simultaneously with ether and water. This mixture was shaken and the aqueous layer was removed. The ether layer was washed with potassium hydroxide (0.1 N, 3×50 milliliters) to remove any unreacted phenol. The ether layer was washed with water (3×50 milliliters) and dried with magnesium sulfate. Filtration afforded a clear solution which was concentrated under diminished pressure to yield 0.70 grams of p-nitroanisole (about 90 percent, melting point 52°–53°. This was shown to be identical with an authentic sample.

EXAMPLE 2

In Situ Methylation of Sodium m-Nitrophenolate with N-methyl, N-nitrosourea in an Organic Solvent The procedure and reactants of Example 1 were used except that sodium m-nitrophenolate was substituted for sodium p-nitrophenolate. 0.6 grams of m-nitroanisole (about 85 percent) were obtained.

EXAMPLE 3

In Situ Methylation of m-Nitrophenol with N-methyl,N-nitrosourea in an Organic/Aqueous Carrier 1.00 grams (7.2 millimoles) of m-nitrophenol and 2.2 grams (21 millimoles) of N-methyl,N-nitrosourea were dissolved in 25 milliliters of a 5:1 mixture of 1,2-dimethoxyethane and water. The solution was placed in an ice bath and treated with 36 milliliters of 0.6 N potassium hydroxide in a dropwise manner. Solvent was removed at reduced pressure and the aqueous layer was extracted with ether. The ether layer was washed (3×50 milliliters) and dried with magnesium sulfate. After workup, 0.27 grams of methyl m-nitroanisole (about 25 percent), a melting point 36°–38°C., were recovered.

EXAMPLE 4

In Situ Methylation of p-Nitrophenol with N-methyl,N-nitrosourea in an Organic/Aqueous Carrier The procedure and reactants of Example 3 were used except that p-nitrophenol was substituted for m-nitrophenol. 0.34 grams of methyl p-nitroanisole were recovered.

EXAMPLE 5

In Situ Methylation of m-Nitrobenzoic Acid with N-methyl,N-nitrosourea in an Organic/Aqueous System 1.00 grams (6 millimoles) of m-nitrobenzoic acid and 2.4 grams (2.4 millimoles) of N-methyl,N-nitrosourea were dissolved in 25 milliliters of a 5:1 mixture of 1,2-dimethoxyethane and water. 40 milliliters of 0.6 N potassium hydroxide was added in a dropwise manner while the mixture was held at 0°C. in an ice bath. The solution was extracted with ether (4×50 milliliters) and the water layer (pH 10) was saved. The ether layer was dried (MgSO₄) and workup gave 0.65 grams of methyl m-nitrobenzoate, melting point 71°–72°C. The water layer gave 0.25 grams of unreacted acid. Yield, based on consumed acid, was approximately 85 percent.

EXAMPLE 6

Methylation of p-Nitrobenzoic Acid with N-methyl,N-nitrosourea in an Organic/Aqueous Carrier The procedure and reactants of Example 5 were used except that p-nitrobenzoic acid was substituted for m-nitrobenzoic acid. 0.75 grams of the ester product were recovered, and the ester had a melting point of 93°–95°C. 0.29 grams of unreacted acid were recovered. Yield, based on consumed acid, was about 97 percent.

EXAMPLE 7

In Situ Methylation of a Mixture of p-Nitrobenzoic Acid and m-Nitrophenol in an Organic/Aqueous Carrier 0.5 grams (3 millimoles) of p-nitrobenzoic acid and 0.41 grams (3 millimoles) of m-nitrophenol were dissolved in 25 milliliters of a 5:1 mixture of 1,2-dimethoxyethane and water. 2.4 grams (24 millimoles) of N-methyl,N-nitrosourea were added to this solution which was then titrated with 40 milliliters of 0.6 N potassium hydroxide at 0°C. The organic layer was removed and the aqueous layer was extracted with ether. The ether layer was dried and removed to yield a mixture of products. Nuclear magnetic resonance analysis revealed the ratio of ester to anisole to be about 7:3, which is the same as that achieved by the independent methylations of each reactant substrate suggesting that both reactions compete independently with water.

EXAMPLE 8

In Situ Methylation of a Mixture of Sodium m-Nitrophenolate and Sodium p-Nitrobenzoate in an Organic Solvent 0.80 grams (5 millimoles) of sodium m-nitrophenolate, 0.945 grams (5 millimoles) of sodium p-nitrobenzoic acid, and 0.52 grams (5 millimoles) of N-methyl,N-nitrosourea were added to 25 milliliters of 1,2-dimethoxyethane, and the mixture was stirred under anhydrous conditions for one hour at 0°C. and subsequently elevated to room temperature for ten hours. The reaction mixture was worked up in the usual manner. Nuclear magnetic resonance analysis revealed the ratio of ester to anisole to be approximately 6:4, suggesting that the reaction is sufficiently slow to allow proton exchange.

EXAMPLE 9

Attempt to React Sodium p-Nitrobenzoate with N-methyl,N-nitrosourea in an Organic Solvent 1.02 grams (5 millimoles) of sodium p-nitrobenzoate and 0.53 grams (5 millimoles) of N-methyl,N-nitrosourea were added to 25 milliliters of 1,2-dimethoxyethane. The mixture was maintained under anhydrous conditions for one hour at 0°C., and then for ten hours at room temperature under constant stirring. The organic layer was removed and the residue was treated simultaneously with 25 milliliters of ether and 25 milliliters of water. The ether layer was washed with a 5% sodium bicarbonate solution (3×25 milliliters) and water (3×75 milliliters). The ether layer was dried using magnesium sulfate and removed under reduced pressure, resulting in a residue found to contain essentially no ester and mostly N-methyl,N-notrosourea.

EXAMPLE 10

Attempt to React Sodium m-Nitrobenzoate with N-methyl,N-nitrosourea in an Organic Solvent The procedure and reactants of Example 9 were used except that sodium m-nitrobenzoate was substituted for sodium p-nitrobenzoate. The same results were obtained, i.e., the residue contained essentially no ester.

EXAMPLE 11

Methylation of p-Nitrobenzoic Acid by Diazomethane Generated by Reacting Sodium Hydride and N-methyl,N-nitrosourea in an Organic Solvent 0.5 grams (5 millimoles) of N-methyl,N-nitrosourea was added to a suspension of 0.11 grams (5 millimoles) of sodium hydride in 15 milliliters of 1,2-dimethoxyethane at 0°C. and under anhydrous conditions. Evolution of hydrogen was observed and the solution slowly turned a bright yellow indicating formation of diazomethane. The solution was decanted and added to an excess of p-nitrobenzoic acid in 1,2-dimethoxyethane. 0.7 grams of the methyl ester of p-nitrobenzoic acid were produced corresponding to a yield of 90 percent, based on limiting diazomethane.

EXAMPLE 12

In Situ Methylation of p-Nitrobenzoic Acid with N-methyl,N-nitrosourea and Triethylamine in an Organic Solvent 0.835 grams (5 millimoles) of p-nitrobenzoic acid and 0.54 grams (5 millimoles) of N-nitroso,N-methylurea were dissolved in 25 milliliters of 1,2-dimethoxyethane and cooled to 0°C. The mixture was then treated with 1.92 milliliters (15 millimoles) of triethylamine and stirred for one hour at 0°C., and then elevated to room temperature and maintained overnight. A precipitate formed which was filtered off. The solvent was concentrated and the residue was dissolved in ether and water followed by extraction of the ether layer with saturated sodium bicarbonate and water; it was then dried over sodium sulfate. Removal of the ether afforded the desired ester in quantitative yield.

Those skilled in the art will know, or be able to ascertain by no more than routine experimentation, many equivalents to the specific embodiments expressly described herein. These are within the scope of this invention and are intended to be covered by the appended claims.

What is claimed is:

1. A process for in situ alkylation of a substrate comprising contacting a source of said substrate with an N-substituted, N-nitrosourea, said source being sufficiently basic to deprotonate said urea, and said urea being represented by the structural formula,

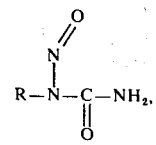

wherein
R represents the group to be added to said substrate and is selected from alkyl; cycloalkyl; heteroalkyl; aralkyl; and, heterocyclic;
whereby a diazo alkylation reagent is generated in the presence of said substrate and the diazo alkylation reagent and substrate react to alkylate said substrate at a rate at least equal to the rate at which said diazoalkyl alkylation reagent is generated so that significant amounts of the diazoalkyl alkylation reagent do not build up.

2. A process of claim 1 wherein said substrate has a pKa of between about 7 and about 16 and wherein said source of said substrate comprises a conjugate base of said substrate.

3. A process of claim 2 wherein R is an alkyl group.

4. A process of claim 3 wherein said alkyl group is methyl and said alkylation reagent which is generated is diazomethane.

5. A process of claim 1 wherein said contacting is accomplished in the presence of an aprotic, neutral, organic solvent.

6. A process of claim 4 wherein said contacting is accomplished in the presence of an aprotic, neutral, organic solvent.

7. A process of claim 6 wherein said solvent is 1,2-dimethoxyethane.

8. A process of claim 5 wherein said contacting is accomplished in the presence of an aqueous medium in addition to the organic medium.

9. A process of claim 1 wherein said substrate has a pKa of below about 7 and wherein said source of said substrate is the combination of said substrate and a nonalkylatable base.

10. A process of claim 9 wherein said base is a trialkylamine.

11. A process of claim 10 wherein said base is triethylamine.

12. A process of claim 11 wherein R is an alkyl group.

13. A process of claim 12 wherein said alkyl group is methyl and wherein said alkylation reagent which is generated is diazomethane.

14. A process for the in situ alkylation of a substrate having a pKa of between about 7 and about 16 comprising contacting a conjugate base of said substrate with an N-substituted, N-nitrosourea which can be represented by the structural formula,

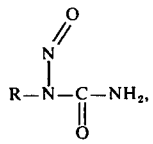

wherein
R represents the group to be added in said substrate and is selected from alkyl; cycloalkyl; heteroalkyl; aralkyl; and, heterocycloalkyl;
whereby a diazo alkylation reagent and the substrate are generated and react at a rate much faster than the rate at which they are generated to thereby achieve alkylation of said substrate.

15. A process of claim 14 wherein R is an alkyl group.

16. A process of claim 15 wherein R is methyl.

17. A process of claim 14 wherein said contacting is accomplished in the presence of an aprotic, neutral, organic solvent.

18. A process of claim 16 wherein said contacting is accomplished in the presence of an aprotic, neutral, organic solvent.

19. A process for in situ alkylation of a substrate having a pKa of below about 7, comprising:
a. contacting said substrate in the presence of an aprotic, neutral, organic solvent with an N-substituted, N-nitrosourea which can be represented by the structural formula:

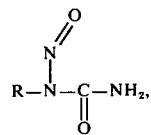

wherein R represents the group to be added to said substrate and is selected from alkyl, cycloalkyl; heteroalkyl; aralkyl; and, heterocycloalkyl; and,
b. adding a base to said mixture, said base being nonalkylatable, whereby said base decomposes said urea to form a diazoalkyl alkylation reagent which reacts with said substrate at a rate at least equal to the rate at which it is generated.

20. A process of claim 19 wherein said base is a trialkylamine.

21. A process of claim 20 wherein R is methyl.

* * * * *